United States Patent
Greenwald et al.

(10) Patent No.: US 6,376,470 B1
(45) Date of Patent: Apr. 23, 2002

(54) POLYMER CONJUGATES OF ARA-C AND ARA-C DERIVATIVES

(75) Inventors: Richard B. Greenwald, Somerset; Yun Hwang Choe, Piscataway, both of NJ (US)

(73) Assignee: Enzon, Inc., Piscataway, NJ (US)

( * ) Notice: Subject to any disclaimer, the term of this patent is extended or adjusted under 35 U.S.C. 154(b) by 0 days.

(21) Appl. No.: 09/404,075

(22) Filed: Sep. 23, 1999

(51) Int. Cl.$^7$ .................. A61K 31/70; C07H 19/19; C07H 19/00

(52) U.S. Cl. .................. 514/43; 514/49; 536/27.4; 536/28.1; 536/28.4; 536/28.5

(58) Field of Search .................. 514/42, 43, 44, 514/49, 50; 536/27.4, 28.1, 28.4, 28.5

(56) References Cited

U.S. PATENT DOCUMENTS

| | | |
|---|---|---|
| 5,122,614 A | 6/1992 | Zalipsky et al. |
| 5,349,001 A | 9/1994 | Greenwald et al. |
| 5,605,976 A | 2/1997 | Martinez et al. |
| 5,641,758 A | 6/1997 | Kluge et al. |
| 5,643,575 A | 7/1997 | Martinez et al. |
| 5,808,047 A | 9/1998 | Kjell |
| 5,808,048 A | 9/1998 | Berglund |
| 5,880,131 A | 3/1999 | Greenwald et al. |
| 5,981,507 A | 11/1999 | Josephson et al. |
| 6,060,592 A | 5/2000 | Acevedo et al. |
| 6,127,355 A | * 10/2000 | Greenwald et al. |

OTHER PUBLICATIONS

Aoshima, M., et al., N4–Behenoyl–1–Beta –D–arabinofuranosylcytosine as a Potential New Antitumor Agent, Cancer Research, vol. 37, p. 2481–2486 (Aug. 1977).

Balajthy, Z, et al., Synthesis and Functional Evaluation of a Peptide Derivative of 1–Beta–D–Arabinofuranosylcytosine, Journal of Medicinal Chemistry, vol. 35, No. 18, p. 3344–3349 (1992).

Duncan, Ruth, Drug–polymer cojugates: potential for improved chemotherapy, Anti–cancer Drugs, vol. 3, p. 175–210 (1992).

Hammer, K. et al., Ether, Carbonate and Urethane Deoxynucleoside derivatives as Prodrugs, Acta Chemica Scandinavica, vol. 50, p. 609–622 (1996).

Hooftman, G. et al., Review: Poly(ethylene glycol)s with Reactive Endgroups. II. Practical Consideration for the Preparation of Protein–PEG Conjugates, Journal of Bioactive and Compatible Polymers, vol. 11, p. 135–159 (Apr. 1996).

Ichikawa, H, et al., Evaluation of the Conjugate Between N4–(4–Carboxybutyryl)–1–Beta–D– Arabinofuranosylcytosine and Chitosan as a Macromolecular Prodrug of 1–Beta– D–Arabinofuranosylcytosine, Drug, Design and Discovery, vol. 10, p. 343–353 (1993).

Kato, Y., et al., Antitumor Activity of 1–Beta–D–Arabinofuranosylcytosine Conjugated with Polyglutamic Acid and Its Derivative, Cancer Research, vol. 44, p. 25–30 (Jan. 1984).

Katre, N.V. The conjugation of proteins with polyethylene glycol and other polymers; Altering properties of proteins to enhance their therapeutic potential, Advanced Drug Delivery Reviews, vol. 10, p. 91–114 (1993).

(List continued on next page.)

*Primary Examiner*—James O. Wilson
(74) *Attorney, Agent, or Firm*—Roberts & Mercanti, LLP

(57) ABSTRACT

The present invention is directed to polymeric-prodrug transport forms of the formula:

(I)

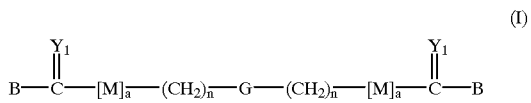

wherein:
G is a linear or branched, terminally functionalized polymer residue;
$Y_1$ is O, S, or $NR_1$;
M is X or Q;
  wherein X is an electron withdrawing group and Q is a moiety containing a free electron pair positioned three to six atoms from $C(=Y_1)$;

B is:

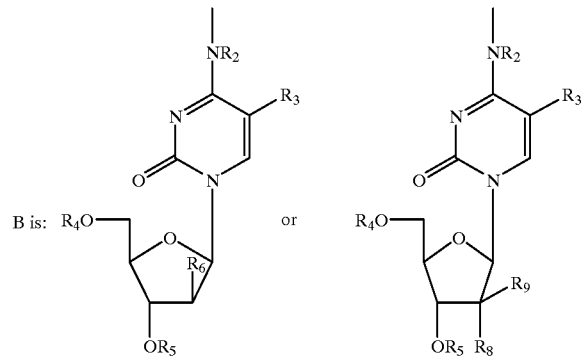

$R_{1-5}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls;

$R_6$ is $OR_7$ or $N_3$, $NH_2$, $NO_2$ or CN, where $R_7$ is selected from the same group which defines $R_{1-5}$;

$R_{8-9}$ are independently selected from the group consisting of hydrogen, fluoro, chloro, bromo, iodo, or $R_6$; and a and n are each independently zero or a positive integer.

Methods of forming and methods of treating using the polymeric-prodrug transport forms disclosed herein are also disclosed.

19 Claims, 2 Drawing Sheets

OTHER PUBLICATIONS

Kawaguchi, T., et al., Steric parameters in PLE catalyzed hydrolysis of N4–substituted cytarabine ester prodrugs (1995). Journal unknown, pages unknown.

Li, C., et al., Complete Regression of Well–established Tumors Using a Novel Water–soluble Poly(L–Glutamic Acid)–Paclitaxel Conjugate, Cancer Research, vol. 58, p. 2404–2409 (Jun. 1, 1998).

Menger, F.M., et al, Synthesis of a Lipid/Peptide/Drug Conjugate: N4–(Acylpeptidyl)–Ara–C, Bioconjugate Chemistry, vol. 5, p. 162–166 (1994).

Ohya, Y., et al., Synthesis and Cytotoxic Activity of Conjugates of Monomethoxy–Poly–(ethylene glycol) End–Capped with Doxorubicin via Ester, Amide, or Schiff's Base Bond, Journal of Bioactive and Compatible Polymers, vol. 10, p. 51–64 (Jan. 1995).

Ouchi, T., et al., Synthesis and Antitumor Activity of Poly-(ethylene glycol)s Linked to 5–Fluorouracil via a Urethane or Urea Bond, Drug, Design and Discovery, vol. 9, p. 93–105 (1992).

Ouchi, T., et al., Syntheses of 5–Flourouracil–Terminated Monomethoxypoly (Ethylene Glycol)s, their Hydrolysis Behavior, and their Antitumor Activities, Copyright 1987 by Marcel Dekker, Inc.

Wipf, P., et al., Prodrugs of ara–C, Drugs of the Future, vol. 19(1), p. 49–54 (1994).

Wipf, P., et al., Synthesis of Chemoreversible Prodrugs of ara–C with Variable Time–Release Profiles. Biological Evaluation of Their Apoptotic Activity, Bioorganic & Medicinal Chemistry, vol. 4, No. 10, p. 1585–1596 (1996).

* cited by examiner

D.

Gemcitabine (9)    PEG-amide-Gemcitabine (10)

POLYMER CONJUGATES OF ARA-C AND ARA-C DERIVATIVES

TECHNICAL FIELD

The present invention relates to polymeric conjugates of anti-metabolites. In particular, the invention relates to polymeric conjugates of ara-C, gemcitabine and derivatives thereof and methods of preparing the same.

BACKGROUND OF THE INVENTION

Ara-C (cytosine arabinose, cytarabine, 1-(β-D-arabinofuranosyl)cytosine) is a pyrimidine nucleotide analog and an effective anticancer drug primarily used in the treatment of acute myelogenous leukemia and some other types of non-solid tumors. One of the chief advantages of ara-C is its ability to block the transition of cells from the G-phase to the S-phase. There are, however, a few shortcomings associated with the molecule as well. For example, ara-C undergoes rapid enzymatic deamination in plasma to form the inactive ara-U by deoxycytidine deaminase. The use of ara-C is also associated with development of resistance and severe toxic side effects caused by large cumulative doses of the drug. Moreover, it is generally thought of as being ineffective in treating solid tumors.

One attempt to address some of the drugs shortcomings has been to administer ara-C in combination with a deaminase inhibitor such as tetrahydro-uridine. Other attempts have centered around controlling deamination such as by modifying the 2-position. Still further proposals have focused on making prodrugs of ara-C. For example, various $N^4$-, 5'- and 3'-acyl derivatives have been proposed as possible ara-C prodrugs.

Prodrugs include chemical derivatives of a biologically-active parent compound which, upon administration, eventually liberate the parent compound in vivo. Prodrugs allow the artisan to modify the onset and/or duration of action of an agent in vivo and can modify the transportation, distribution or solubility of a drug in the body. Typical examples of prodrugs include organic phosphates or esters of alcohols or thioalcohols (thiols).

One type of ara-C prodrug is based on $N^4$-peptidyl derivatives. See, for example, F. M. Menger et al. *Bioconjugate Chem.* 5, 162 (1994); Wipf, P. et al. *Bioorganic & Medicinal Chemistry* vol. 4, No. 10, pp 1585–1596 (1996); and Balajthy et al. *J. Med. Chem.* 35, pp. 3344–3349 (1992). Similarly, U.S. Pat. No. 5,641,758 discloses $N^4$-octadecyl ara-C derivatives which have allegedly improved resistance to enzymatic deamination. Although $N^4$-octadecyl prodrugs release the ara-C in vivo, it would be beneficial if the circulating life and activity against solid tumors could be enhanced.

Polymeric conjugation has been suggested as a means to improve the pharmacokinetic and pharmacodynamic properties of a parent drug compound. For example, U.S. Pat. No. 5,880,131 to Greenwald et al., the contents of which are incorporated herein by reference, discloses ester-based polymeric attachment to temporarily increase the circulating life of a parent drug. Relatively hydrolysis-resistant linkages between the polymer and the parent compound residue are not disclosed.

Although some polymer-ara-C conjugates have been reported, they are believed to have exhibited one or more drawbacks. One approach taken to synthesize polymeric drugs of ara-C is found in *J. Cancer Research* 44, 25–30, January (1984). The authors conjugated either polyglutamic acid (PLGA) or a related copolymer (PHEG) to the $N^4$ position of ara-C via an amide linkage. The degree of loading onto the pendant groups of the copolymers, however, is unpredictable and can only be estimated. The location of the ara-C molecules on the copolymers is also random. Thus, it is not surprising that the rate of hydrolysis of the ara-C from these polymers is unpredictable and that the amount of ara-C released from the copolymers is also variable. Further, although the authors reported that these compounds had superior in vitro activity in an L1210 (leukemia) cell line when compared to ara-C, no activity was reported with regard to their effectiveness on solid tumors.

Another approach to forming ara-C prodrugs is reported by Ichikawa, H. et al. in *Drug Design and Discovery*, 1993, Vol. 10, pp. 343–353. In this case, chitosan (a biodegradable polymer with repeating pendant groups) is linked to ara-C via a glutaric anhydride spacer. The reactions, however, are low yield and, like the PLGA and PHEG conjugates of ara-C described above, the chitosan-spacer-ara-C conjugates suffer from the same unpredictable loading on the pendant groups and subsequently hydrolysis of the ara-C.

Thus, in spite of the advances already made with ara-C, there continues to be a need for further improvements. The present invention addresses this need.

SUMMARY OF THE INVENTION

In one aspect of the invention, compounds of Formula (I) are provided:

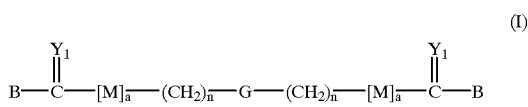

wherein:
G is a linear or branched terminally functionalized polymer residue;
$Y_1$ is O, S, or $NR_1$;
M is selected from either X or Q;
  wherein X is an electron withdrawing group and Q is a moiety containing a free electron pair positioned three to six atoms from $C(=Y_1)$;

B is: 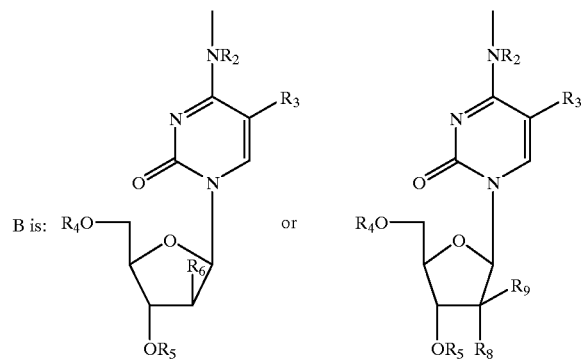

$R_{1-5}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls;
$R_6$ is $OR_7$ or $N_3$, $NH_2$, $NO_2$ or CN, where $R_7$ is selected from the same group as that which defines $R_{1-5}$;

$R_{8-9}$ are independently selected from the group consisting of hydrogen, fluoro, chloro, bromo, iodo, or $R_6$; and a and n are each independently zero or a positive integer, preferably from about 1 to about 5.

In preferred embodiments, $Y_1$ is O, G is a poly(ethylene glycol) residue, and M is either NH or oxygen.

For purposes of the present invention, the term "residue" shall be understood to mean that portion of a biologically active compound which remains after the biologically active compound has undergone a substitution reaction in which the prodrug carrier portion has been attached.

For purposes of the present invention, the term "alkyl" shall be understood to include straight, branched, substituted, e.g. halo-, alkoxy-, and nitro-$C_{1-12}$ alkyls, $C_{3-8}$ cycloalkyls or substituted cycloalkyls, etc.

For purposes of the present invention, the term "substituted" shall be understood to include adding or replacing one or more atoms contained within a functional group of compound with one or more different atoms. The term "sufficient amounts" for purposes of the present invention shall mean an amount which achieves a therapeutic effect as such effect is understood by those of ordinary skill in the art.

One of the chief advantages of the polymer conjugates of the present invention is the fact that the ara-C residues are only found on the termini of the polymer. The uniform polymeric conjugates are thus easy to analyze and are highly reproducible. The rate of hydrolysis is also predictable and reproducible from batch to batch. Still, a further advantage is that in certain preferred embodiments, in which the polymer portion has a molecular weight of from about 20 to about 50 kDa, the conjugates are believed to passively target tumors and thus enhance the effectiveness of ara-C and related compounds on solid tumors. While applicants are not bound by theory, it is believed that tumor proteases, alone and/or in combination with peptidases, cleave the aromatic amide or carbamate bonds, thus freeing the parent active agent within the tumor. Methods of making and using the compounds and conjugates described herein are also provided.

DETAILED DESCRIPTION OF THE INVENTION

A. Ara-C Derivatives

Figure 1:
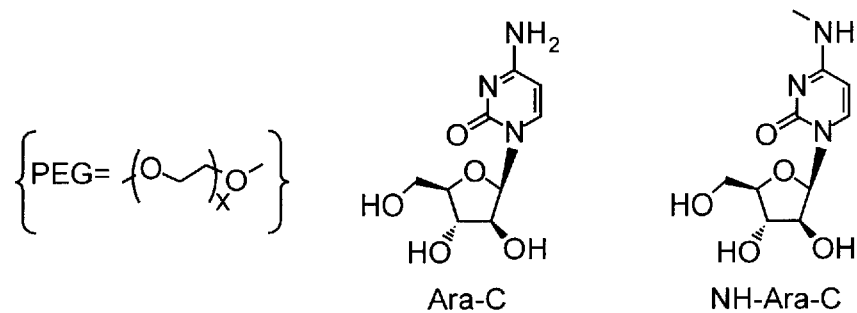
FIGS. 1–2 schematically illustrates the synthesis of compounds described in the specification.
Figure 1:
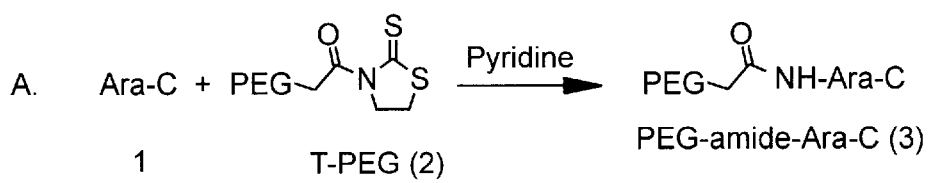
Figure 1:
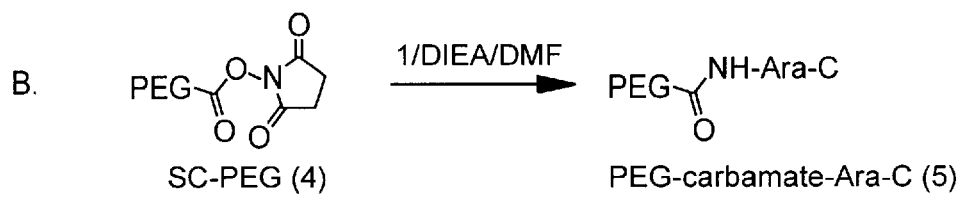
Figure 1:
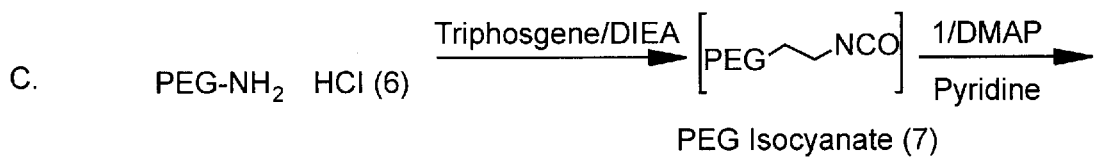
Figure 1:
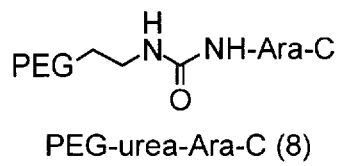

In formula (I), B is one of:

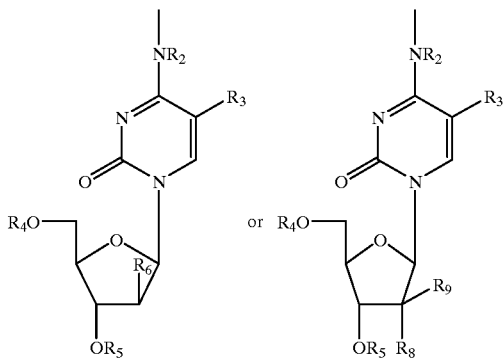

wherein all variables are as defined above in the Summary of the Invention section. In some preferred embodiments, B is an ara-C residue in which $R_{2-5}$ are each hydrogen and $R_6$ is $OR_7$, where $R_7$ is also hydrogen. The ara-C residue has the structure:

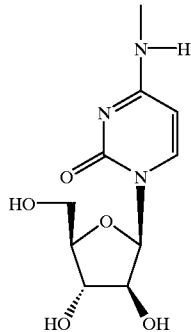

In other preferred embodiments, B is a gemcitabine residue in which each of $R_{2-5}$ is hydrogen, and each of $R_8$ and $R_9$ is fluoro-. The residue has the structure:

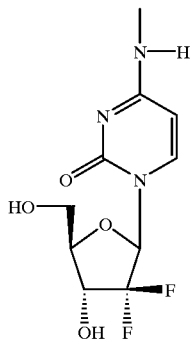

In alternative aspects of the invention, B is a residue of an ara-C derivative such as those described in "Prodrugs of ara-C", by Wipf, P. et al. in *Drugs of the Future.* (1994) 19(1): 49–54, the contents of which are incorporated herein by reference. For example, B can be a 5' or 3'-acyl ara-C derivative residue, a cyclocytidine residue or 2'-deoxycytidine derivative residue. For purposes of the present invention, it will be understood that the residue of the ara-C moiety is designed for covalent attachment via the $N^4$ substituent thereof. It will be further understood by those of ordinary skill that the invention embraces not only the ara-C derivatives specifically mentioned herein but also any others capable of undergoing $N^4$- polymeric substitution reactions.

B. Substantially Non-antigenic Polymers

Within formula (I), G is a linear or branched terminally functionalized polymer residue which is preferably substantially non-antigenic. In preferred aspects of the invention, the polymer residue is based on polyalkylene oxides such as poly(ethylene glycol) (PEG). The general formula for PEG and its derivatives, i.e.

$$A'-O-(CH_2CH_2O)_x-A$$

where (x) represents the degree of polymerization (i.e. from about 10 to about 2,300) or number of repeating units in the polymer chain and is dependent on the molecular weight of the polymer, (A) is H or a capping group such as aminoalkyl, carboxyalkyl, haloalkyl, or other activating group and (A') is the same as (A) or another (A) moiety. In alternative aspects, the polymer residue is a poly(propylene glycol) (PPG). Thus, the G moiety residues are preferably O—(CH$_2$CH$_2$O), or O—(CH(CH$_3$)CH$_2$O)$_x$, wherein x is the degree of polymerization. Also useful are branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998". The disclosure of each of the foregoing is incorporated herein by reference.

As an alternative to the preferred PAO-based polymers, other effectively non-antigenic, terminally functionalized polymers such as dextran, polyvinyl alcohols and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" and "substantially non-antigenic" shall be understood to include all polymeric materials understood in the art as being substantially non-toxic and not eliciting an appreciable immune response in mammals. It will be understood by those of ordinary skill that the water-soluble polymer, e.g. PEG, can be terminally functionalized using standard organic synthesis techniques which are reported in the literature to add the desired spacer-liner moiety and leaving group for facilitating attachment to the ara-C derivative NH group. Alternatively, functionalized PEG's are available from commercial suppliers such as Shearwater Polymers of Huntsville, AL or Aldrich Chemical Company of Milwaukee, Wis. Thus, the PEG can be terminally modified to include moieties of the formula (II):

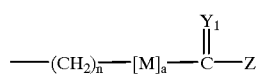

(II)

wherein all of the variables are as set forth above with the exception of Z which is a leaving group, such as an activated carbonate moiety like p-nitrophenyl or succinimidyl carbonate; a thiazolidine thione or other art recognized activating group which is capable of reacting with an unprotected amine. In the final synthesis step, the ara-C moiety is reacted with the polymer to form the conjugate.

In order to provide the desired linkage, activated polymers such as PEG diacids can be used as well as PEG diamines and PEG diols. Suitable PAO acids can be synthesized by first converting PEG-OH to an ethyl ester followed by saponification. See also Gehrhardt, H., et al. *Polymer Bulletin* 18:487 (1987) and Veronese, F. M., et al., *J. Controlled Release* 10; 145 (1989). Alternatively, the PAO-acid can be synthesized by converting PEG-OH into a t-butyl ester followed by acid cleavage. See, for example, commonly assigned U.S. Pat. No. 5,605,976. The disclosures of each of the foregoing are incorporated by reference herein. Although PAO's and PEG's can vary substantially in number average molecular weight, polymers ranging from about 2,000 to about 100,000 are usually selected for the purposes of the present invention. Molecular weights of from about 5,000 to about 80,000 are preferred and 20,000 to about 50,000 are particularly preferred. The number average molecular weight of the polymer selected for inclusion in the prodrug must be sufficient so as to provide sufficient circulation of the prodrug before hydrolysis of the linker. Preferably, G is O—(CH$_2$CH$_2$O)$_x$ and x is a positive integer selected so that the number average molecular weight is at least about 20,000 Daltons.

C. The Linkage Moieties

1. The M Groups

Within the Formula (I), M is X or Q wherein X and Q are variables which represent electron withdrawing groups. In particular, X and Q can be independently selected from moieties such as O, S, or NR$_{10}$ wherein R$_{10}$ is one of hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls and substituted C$_{1-6}$ heteroalkyls, branched, alkyls, aryls, substituted aryls, C$_{1-6}$ alkyl aralkyls, heteroalkyls, substituted heteroalkyls or substituted C$_{1-6}$ alkyls such caraboxyalkyls, aminoalkyls, dialkylaminos, hydroxyalkyls or mercaptoalkyls, to name but a few. Preferably, X is either O or NR$_{10}$ and R$_{10}$ is preferably H.

2. Q Portion of the Linker

When M is Q, the polymer residue G is preferably attached to Q via a heteroatom such as oxygen. Q is a moiety containing a free electron pair positioned three to six atoms from the C(=Y$_1$) moieties. In a preferred embodiment, the free electron pair is five atoms from the C(=Y$_1$) moieties. Q can be selected from the non-limiting list of cycloalkyls, aryls, aralkyl groups substituted with O, S or NR$_{11}$, where R$_{11}$, is defined as the same group as that listed above with regard to R$_{10}$. Preferably, R$_{11}$ is H, a C$_{1-6}$ alkyl or substituted C$_{1-6}$ alkyl. The free electron pair can be anywhere along the Q moiety as long as the defined spacing between the free electron pair and the C(=Y$_1$) is maintained. Thus, Q assists hydrolysis of the prodrug linkage by anchimeric assistance because the free electron pair can generate a three- to six-membered, but preferably five-membered, ring intermediate upon hydrolysis preferably of the ester linkage.

D. Synthesis of Polymeric Prodrug Transport System

The prodrugs of the present invention can be prepared using standard organic synthesis techniques. If necessary, the spacer is attached to the polymer and activated by attaching a terminal leaving group. The activated polymer portion can be obtained from either commercial sources or synthesized by the artisan without undue experimentation. For example, PEG-diacids are available from Shearwater Polymers of Huntsville, AL or Aldrich Chemical Company of Milwaukee, Wis. They can also be synthesized as described in commonly assigned U.S. Pat. No. 5,605,976, the contents of which are incorporated herein by reference. When amide linkages are sought, an activated PEG such as a bis-thiazolidine-2-thione-activated PEG (T-PEG) such as that described in commonly assigned U.S. Pat. No. 5,349, 001 can be used. Alternatively, when a carbamate linkage is sought, a suitably activated PEG such as PEG-dichloroformate or bis-SC-PEG, prepared as described in commonly assigned U.S. Pat. No. 5,122,614, or a bis-p-nitrophenyl chloroformate-activated PEG can be used. The disclosure of each of the two mentioned U.S. patents are incorporated herein by reference. The urea-linked ara-C can be prepared using bis-PEG-isocyanate generated by reacting bis-PEG-NH$_2$ with phosgene or triphosgene and a tertiary base such as diisopropylethylamine (DIEA). Regardless of the source, the activated polymer is then reacted with the ara-C derivative to form the conjugate.

For purposes of illustration, the methods include reacting a compound of the structure (III)

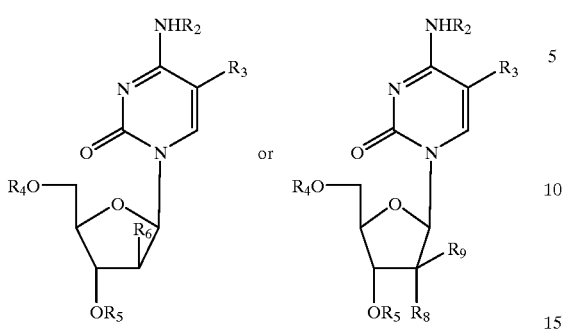

(III)

with a bis terminally activated polymer of the formula (IV)

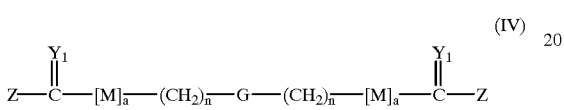

Figure 2:
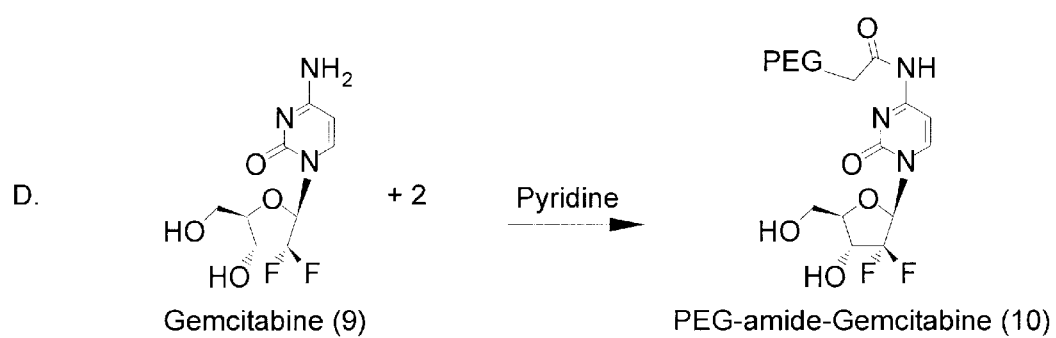

(IV)

to form the compositions of formula (I). See also FIGS. 1 and 2 for reaction schemes related hereto.

Attachment of the B moiety, i.e. the ara-C derivative, can also be carried out in the presence of a coupling agent. A non-limiting list of suitable coupling agents includes 1,3-diisopropylcarbodiimide DIPC), any suitable dialkyl carbodiimides, 2-halo-1-alkyl-pyridinium halides, (Mukaiyama reagents), 1-(3-dimethylamino-propyl)-3-ethyl carbodiimide (EDC), 1-propanephosphonic acid cyclic anhydride (PPACA) and phenyl dichlorophosphates, etc. which are available, for example, from commercial sources such as Sigma-Aldrich Chemical, or synthesized using known techniques. Preferably EDC is used in pyridine to couple the ara-C derivative with PEG-carboxylic acid. Alternatively, a PEG-carboxylic activated imide, T-PEG, is reacted with ara-C in pyridine to produce the desired conjugate (prodrug). Other inert solvents such as methylene chloride, chloroform, toluene, DMF or mixtures thereof can also be used. The reaction is also preferably conducted at a temperature from 20° C. up to about 45° C., in the presence of a base, such as 4-(dimethylamino)pyridine, diisopropylethylamine, pyridine, triethylamine, etc. to neutralize any acids generated. Regardless of the synthesis selected, some of the preferred compounds which result from the synthesis techniques described herein include:

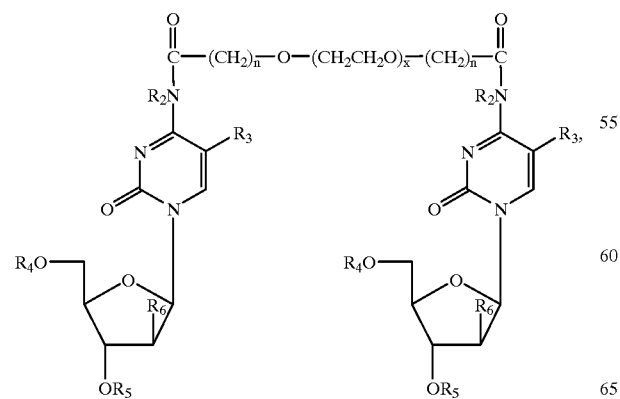

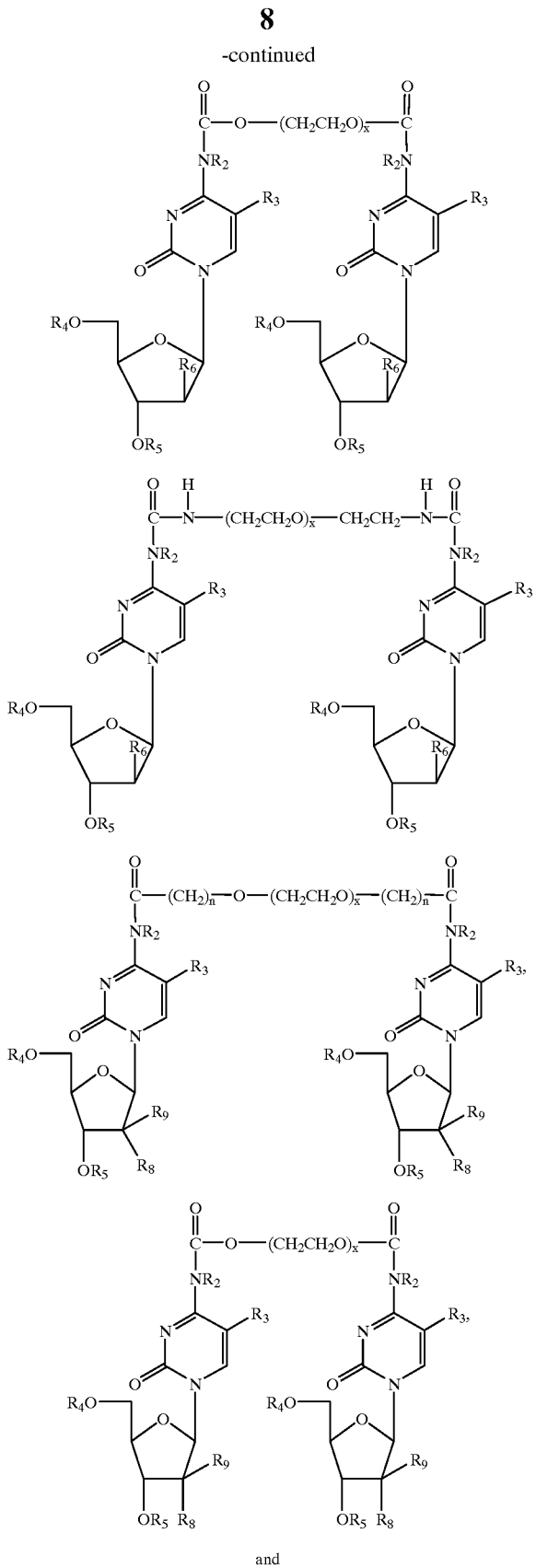

and

-continued

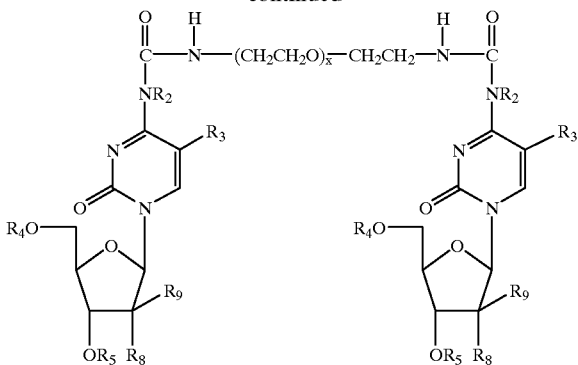

where x represents the degree of polymerization.

E. Method of Treatment

Another aspect of the present invention provides methods of treatment for various medical conditions in mammals. The methods include administering to the mammal in need of such treatment, an effective amount of a polymer conjugate, such as an ara-C-PEG conjugate, which has been prepared as described herein. The compositions are useful for, among other things, treating neoplastic disease including leukemias, reducing tumor burden, preventing metastis of neoplasms and preventing recurrences of tumor/neoplastic growths in mammals.

The amount of the polymer conjugate administered will depend upon the specific ara-C molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, prodrug ara-C is administered in amounts ranging from about 5 to about 5,000 mg/m² per day, based on the amount of the ara-C moiety. Gemcitabine polymer conjugates prodrugs are also administered in amounts ranging from about 5 to about 2,000 mg/m² per day. The range set forth above is illustrative and those skilled in the art will determine the optimal dosing of the selected prodrug based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may be also be by infusion into a body space or cavity, as well as by inhalation and/or intranasal routes. In preferred aspects of the invention, however, the prodrugs are parenterally administered to mammals in need thereof.

F. EXAMPLES

The following examples serve to provide further appreciation of the invention but are not meant in any way to restrict the effective scope of the invention. The underlined and bold-faced numbers recited in the Examples correspond to those shown in the Figures.

All reactions were run under atmosphere of dry nitrogen or argon. Commercial reagents were used without further purification. Ara-C was obtained from Sigma Chemical Compound (Madison, Wis.) and t-Boc protected amino acids were from Advanced ChemTech (Louisville, Ky.). All PEG compounds were dried under vacuum or by azeotropic distillation from toluene prior to use.

The HPLC Method

Analytical HPLC's were performed using a C8 reverse phase column (Beckman, ultrasphere) under isocratic conditions with a 80:20 mixture (v/v) of methanol-water as the mobile phase. Peak elutions were monitored at 254 nm using UV detector. To detect the presence of any free PEG and also to confirm the presence of PEGylated product, an evaporative light scattering detector (ELSD), Model PL-EMD 950 (Polymer Laboratories), was employed. Based on ELSD/uv analysis, all the final PEGylated products were free of native ara-C and were ≧95% pure by HPLC.

Analysis of Ara-C Contents in PEG Derivatives

For the determination of ara-C contents in PEG derivatives, $N^4$-acetylcytidine was used as the standard because of the absorbance change due to the acylation of ara-C. The UV absorbance of $N^4$-acetylcytidine in water was determined at 257 nm for six different concentrations ranging from 0.01 μmol/mL to 0.05 μmol/mL. From the standard plot of absorbance vs. concentration, the absorption coefficient, ε, of $N^4$-acetylcytidine was calculated to be 36.4 (O.D. at 257 nm for 1 mg/mL with 1.0 cm light path). PEGylated ara-C derivatives were dissolved in water at an approximate concentration of 0.015 mmol/mL (based on MW of 40 kDa) and the UV absorbance of these compounds at 257 nm was determined. Using this value and employing the absorption coefficient, ε, obtained from the above, the concentration of ara-C in the sample was determined. Dividing this value by the sample concentration provided the percentage of ara-C in the sample.

Example 1

PEG-amide-Ara-C (3)

A mixture of ara-C (1, 20 mg, 0.082 mmol) and T-PEG (2, 40 kDa, 0.5 g, 0.013 mmol) in anhydrous pyridine (10 mL) was stirred at 40° C. overnight. The reaction mixture was concentrated in vacuo and the residue was recrystallized from 2-propanol (IPA, 100 mL) to give 0.48 g (96%) of product as a white solid. The amount of ara-C present in this compound as measured by UV assay was 1.07% by weight: $^{13}C$ NMR (67.80 MHz, CDCl3) δ61.06, 69.77–70.74 (PEG), 74.36, 85.21, 87.30, 94.63, 146.35, 153.58, 161.35, 169.23.

Example 2

PEG-carbamate-Ara-C (5)

DIEA (60 μL, 0.35 mmol) is added to a mixture of SC-PEG 40 kDa (4, 1.0 g, 0.025 mmol) and 1 (0.15 g, 0.5 mmol) in DCM (10 mL) and DMF (10 mL) and the mixture is stirred overnight at room temperature. The solvent is removed in vacuo and the residue is recrystallized from IPA to give PEG-carbamate-Ara-C (5).

Example 3

PEG-urea-Ara-C (8)

A solution of PEG-diamine dihydrochloride (6), (3.0 g, 0.08 mmol) in 80 mL of toluene is azeotroped for 2 hours.

The solution is cooled to 30° C. followed by the addition of triphosgene (0.02 g, 0.06 mmol) and DIEA (0.07 g, 0.5 mmol). This mixture is stirred for 3 hours at 70–80° C. followed by cooling to room temperature and addition of 60 mL of ethyl ether. PEG-isocyanate (7) is collected by filtration under nitrogen, and immediately added to a solution of 1 (0.27 g, 1.1 mmol) and DMAP (0.14 g, 1.1 mmol) in anhydrous pyridine (30 mL) and the reaction is stirred at 45° C. overnight. The solvent is removed in vacuo, and the residue is crystallized from IPA to yield PEG-urea-Ara-C (8).

Example 4

PEG-amide-Gemcitabine (10)

A mixture of gemcitabine (9, 261 mg, 0.99 mmol) and 2 (40 kDa, 5 g, 0.13 mmol) in anhydrous pyridine (50 mL) was stirred at 40° C. overnight. The reaction mixture was concentrated in vacuo and the residue was recrystallized from IPA (400 mL) to give 4.8 g (96%) of product as a white solid. The amount of gemcitabine present in this compound as measured by UV assay similar to the ara-C assay was 0.93% by weight: $^{13}$C NMR (67.80 MHz, CDCl$_3$) δ58.62, 67.73, 68.23, 69.91–70.84 (PEG), 71.93, 78.36, 81.00, 95.79, 122.04, 144.66, 154.34, 161.22, 169.59.

(MTD) of 100 mg/kg/dose. Therefore, this study compares the PEG-conjugate at one fifth the native dose, and presumably much less than its MTD. Mouse weight and tumor size were measured at the beginning of study and twice weekly through week 4. Drug effectiveness were determined by comparing tumor growth in treated versus untreated (no vehicle) control mice. Five types of endpoints were used as the basis for comparison: (a) mean tumor volumes at day 24; (b) mean percent change in individual tumor volumes from initial; (c) percent difference in tumor volume (%T/C), measured when the control group's median tumor volume reached approximately 800–1100 mm$^3$ (exponential growth phase); (d) percent difference in tumor volume (%T/C) at day 24 and (e) the number of tumor regression (smaller tumor volume on day 24 compared to day 1) per group.

Results

Native ara-C appeared ineffective in this solid tumor model. In contrast, at one fifth of the unmodified or native dose, PEG-ara-C caused significant tumor growth inhibition (Table 1). PEG-ara-C treatment resulted in lower mean tumor volumes, smaller increases in tumor size and more tumor regressions as compared to both control and native ara-C.

TABLE 1

Efficacy comparison between Ara-C and PEG-AraC$^\alpha$ against subcutaneous human non-small cell lung carcinoma$^\beta$ (LX-1) in Nude mice

|  | Total Dose (mg/kg) | Mean Vol. ± SEM at Day 24 | % Change ± SEM at Day 24 | T/C (%)$^\delta$ at Day 7 | T/C (%)$^\delta$ at Day 24 | Regression at Day 24 (#/Grp) | Complete Regression (#/Grp) |
|---|---|---|---|---|---|---|---|
| Control | 0 | 3131.8 ± 258.7 | 1035.8 ± 258.7 | — | — | 0/7 | 0/7 |
| Ara-C | 400 | 3192.5 ± 369.1 | 1514.8 ± 369.1 | 112.2 | 144.6 | 0/7 | 0/7 |
| PEG-Ara-C | 80 | 2205.0 ± 202.9 | 557.4 ± 202.9* | 76.4 | 73.0 | 1/6 | 1/6 |

$^\alpha$All PEG compounds were given 2x/week for 2 weeks, i.v.
$^\beta$Mean baseline tumor volume was 300 mm$^3$.
$^\delta$The median tumor volume of treatment and control groups were measured and compared when the control group's median tumor volume reached approximately 1000 mm$^3$ (day 7) and 2400 mm$^3$ (day 24).
*Significant (P < 0.05) vs Ara-C Example 5

In vivo Experiment

Athymic nude mice were implanted subcutaneous with a 4–5 mm$^3$ tissue fragment of LX-1 collected from donor mice. The tumor trocar site was observed twice weekly and measured once palpable. The tumor volume for each mouse was determined by measuring two dimensions with calipers and calculated using the formula: tumor volume=(length× width$^2$)/2. When tumors reached the average volume of 300 mm$^3$, the mice were divided into their experimental groups, which consisted on untreated control, unmodified Ara-C and PEG-Ara-C. The mice were sorted to evenly distribute tumor size, grouped into 6 to 7 mice per group, and ear punched for permanent identification. Drugs were administered intravenously every 3 days×4 doses (day 1, 4, 7 and 10) via the tail vein at an approximate rate of 0.5 mL per minute. Due to volume constraints Ara-C and its conjugated derivative were not given on an equal molar basis (absolute amount of active). Instead, the PEG conjugate was administered at individual doses of 20 mg/kg, while the parent compound was given close to its maximum tolerated dose Example 6

In vitro Experiment

Cell Lines and Cytotoxicity Assays. Studies using P388/0 cell lines for IC$_{50}$ (drug concentration inhibiting growth of cells by 50%) were maintained and conducted using standard procedures. Briefly, for IC$_{50}$ determination, cells were seeded into the microwell plates at a density of 2×10$^3$ cells per 50 μL per well. Plates were incubated at 37° C. in a humidified incubator with 5% CO$_2$ for 3 days. Cell growth was measured by the addition of 10 μL/well of Alamar Blue (Alamar Biosciences, Inc., Sacramento, Calif.) and the plates were incubated a further 4 hours at 37° C. The IC$_{50}$ values for each compound were determined from absorbance versus dilution factor plots. All cell cultures for animal implantation were maintained at 37° C. in a humidified atmosphere of 5% CO$_2$/95% O$_2$ and subcultured once a week. All cell lines were periodically tested for Mycoplasma and were Mycoplasma free. The results are shown in Table 2.

TABLE 2

In vitro result of Ara-C, Gemcitabine and Their PEG Derivatives.

| Compound | IC50 (P388/0, nM) |
|---|---|
| Ara-C | 10 |
| PEG-Ara-C | 12 |
| Gemcitabine | 2 |
| PEG-Gemcitabine | 46 |

While there have been described what are presently believed to be the preferred embodiments of the invention, those skilled in the art will realize that changes and modifications may be made without departing from the spirit of the invention. It is intended to claim all such changes and modifications as fall within the true scope of the invention. Numerous references are cited in the specification, the disclosures of all of which are incorporated by reference in their entireties.

We claim:

1. A compound comprising the formula:

$$B-\overset{Y_1}{\overset{\|}{C}}-[M]_a-(CH_2)_{\overline{n}}-G-(CH_2)_{\overline{n}}-[M]_a-\overset{Y_1}{\overset{\|}{C}}-B \quad (I)$$

wherein:

G is a linear or branched, terminally functionalized polymer residue;

$Y_1$ is O, S, or $NR_1$;

M is X or Q;

wherein X is an electron withdrawing group and Q is a moiety containing a free electron pair positioned three to six atoms from $C(=Y_1)$;

B is:

[chemical structures]

$R_1$, $R_2$, $R_3$, $R_4$ and $R_5$ are independently selected from the group consisting of hydrogen, a $C_{1-6}$ alkyl, a $C_{3-12}$ branched alkyl, a $C_{3-8}$ cycloalkyl, a $C_{1-6}$ substituted alkyl, a $C_{3-8}$ substituted cycloalkyl, an aryl, a substituted aryl, an aralkyl, a $C_{1-6}$ heteroalkyl or a substituted $C_{1-6}$ heteroalkyl;

$R_6$ is $OR_7$ or $N_3$, $NH_2$, $NO_2$ or CN, where $R_7$ is selected from the same group which defines $R_{1-5}$;

$R_{8-9}$ are independently selected from the group consisting of hydrogen, fluoro, chloro, bromo, iodo, or $R_6$; and a and n are each independently zero or a positive integer.

2. The compound of claim 1, wherein $Y_1$ is oxygen.

3. The compound of claim 1, wherein n is zero, one or two.

4. The compound of claim 3, wherein n is zero.

5. The compound of claim 3, wherein n is one.

6. The compound of claim 3, wherein n is two.

7. The compound of claim 1, wherein a is zero.

8. The compound of claim 1, wherein a is one.

9. The compound of claim 1, wherein M is NH.

10. The compound of claim 1, wherein a and n are both zero.

11. The compound of claim 1, wherein B is

[chemical structure]

12. The compound of claim 1, wherein B is

[chemical structure]

13. The compound of claim 1, wherein G is $O-(CH_2CH_2O)_x$ or $O-(CH(CH_3)CH_2O)_x$, where in x is a positive integer selected so that the number average molecular weight is at least about 20,000 Daltons.

14. The compound of claim 13, wherein G has a number average molecular weight of from about 20,000 Daltons to about 100,000 Daltons.

15. The compound of claim 14, wherein G has a number average molecular weight of from about 25,000 Daltons to about 60,000 Daltons.

16. A compound of claim 1, selected from the group consisting of:

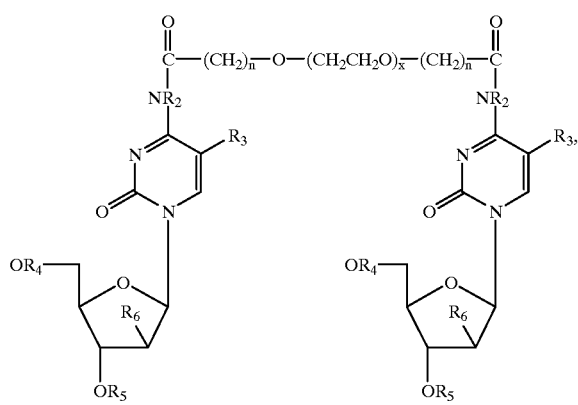

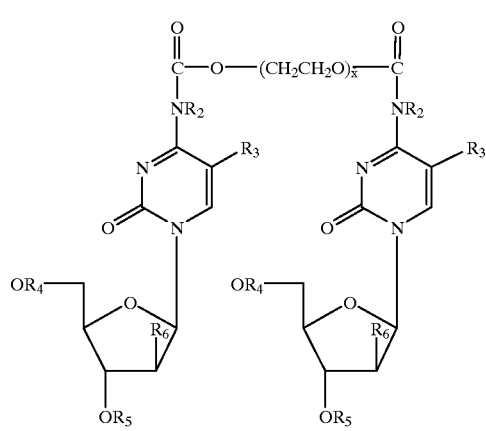

and

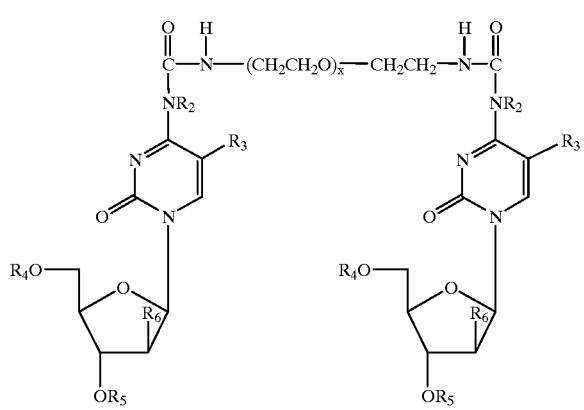

wherein x is a positive integer selected so that the number average molecular weight is at least about 20,000 Daltons.

17. A compound of claim 1, selected from the group consisting of:

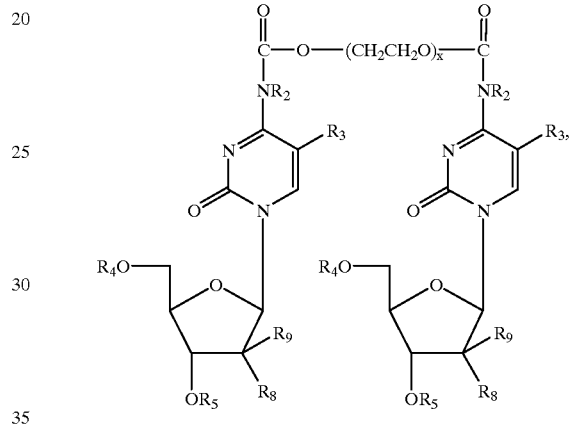

and

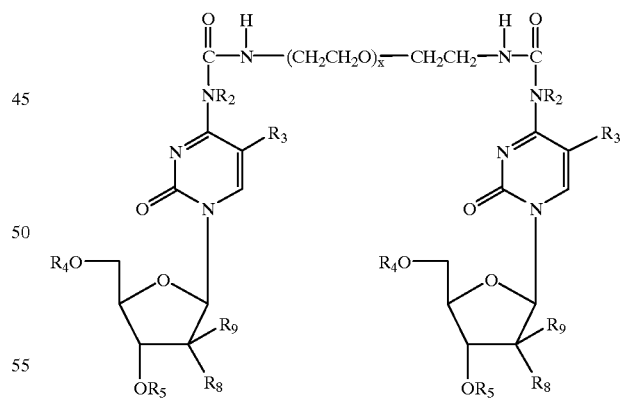

wherein x is a positive integer selected so that the number average molecular weight is at least about 20,000 Daltons.

18. A method of treating neoplastic disease in mammals comprising administering to a mammal in need of such treatment an effective amount of a composition of claim 1.

19. A method of preparing polymeric conjugates, comprising reacting a compound selected from the group consisting of:

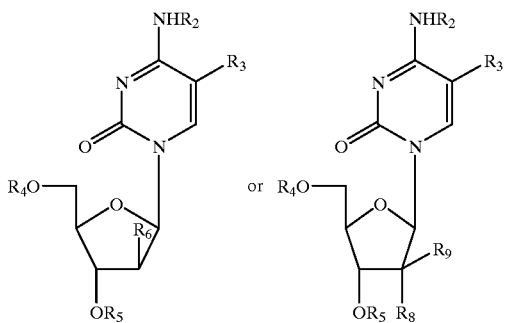

wherein $R_2$, $R_3$, $R_4$ and $R_5$ are independently selected from the group consisting of hydrogen, a $C_{1-6}$ alkyl, a $C_{3-12}$ branched alkyl, a $C_{3-8}$ cycloalkyl, a $C_{1-6}$ substituted alkyl, a $C_{3-8}$ substituted cycloalkyl, an aryl, a substituted aryl, an aralkyl, a $C_{1-6}$ heteroalkyl or a substituted $C_{1-6}$ heteroalkyl;

$R_6$ is $OR_7$ or $N_3$, $NH_2$, $NO_2$ or CN, where $R_7$ is selected from the same group as that which defines $R_{1-5}$;

$R_{8-9}$ are independently selected from the group consisting of hydrogen, fluoro, chloro, bromo, iodo, or $R_6$;

with a bis terminally activated polymer of the formula (IV):

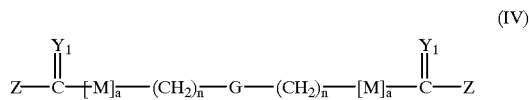

wherein

G is a linear or branched, terminally functionalized polymer residue;

$Y_1$ is O, S, or $NR_1$;

M is X or Q;

wherein X is an electron withdrawing group and Q is a moiety containing a free electron pair positioned three to six atoms from $C(=Y_1)$;

Z is a leaving group; and a and n are each independently zero or a positive integer, whereby a polymeric conjugate is formed.

* * * * *

UNITED STATES PATENT AND TRADEMARK OFFICE
CERTIFICATE OF CORRECTION

PATENT NO. : 6,376,470 B1
DATED : April 23, 2002
INVENTOR(S) : Greenwald, R.B. et al.

It is certified that error appears in the above-identified patent and that said Letters Patent is hereby corrected as shown below:

Column 14,
Line 4, delete "Y", insert -- $Y_1$ --;
Line 54, delete "where in", insert -- wherein --;
Line 66, et seq.: delete

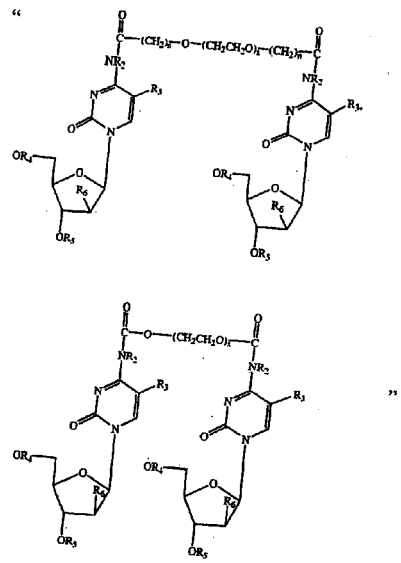

UNITED STATES PATENT AND TRADEMARK OFFICE
CERTIFICATE OF CORRECTION

PATENT NO. : 6,376,470 B1
DATED : April 23, 2002
INVENTOR(S) : Greenwald, R.B. et al.

It is certified that error appears in the above-identified patent and that said Letters Patent is hereby corrected as shown below:

Column 14, cont'd,
Line 66, insert

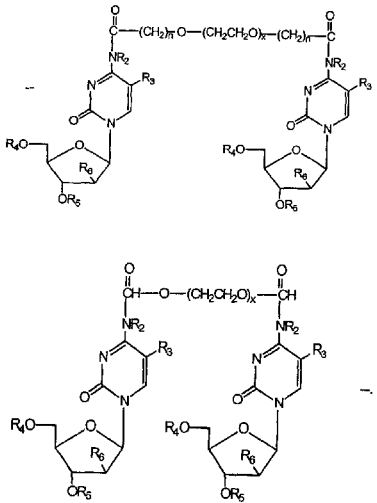

Signed and Sealed this

Seventh Day of October, 2003

JAMES E. ROGAN
*Director of the United States Patent and Trademark Office*